(12) United States Patent
Al Alawi et al.

(10) Patent No.: US 10,828,311 B2
(45) Date of Patent: Nov. 10, 2020

(54) CONTROLLED RELEASE COMPOSITIONS AND THEIR METHODS OF USE

(71) Applicant: BAYER NEW ZEALAND LTD, Hamilton (NZ)

(72) Inventors: Fadil Al Alawi, Auckland (NZ); Olaf Bork, Hamilton (NZ); Ian George Tucker, Hamilton (NZ)

(73) Assignee: BAYER NEW ZEALAND LIMITED, Hamilton (NZ)

( * ) Notice: Subject to any disclaimer, the term of this patent is extended or adjusted under 35 U.S.C. 154(b) by 461 days.

(21) Appl. No.: 14/380,902

(22) PCT Filed: Feb. 27, 2013

(86) PCT No.: PCT/NZ2013/000022
§ 371 (c)(1),
(2) Date: Aug. 25, 2014

(87) PCT Pub. No.: WO2013/129944
PCT Pub. Date: Sep. 6, 2013

(65) Prior Publication Data
US 2015/0045337 A1    Feb. 12, 2015

(30) Foreign Application Priority Data

Feb. 27, 2012 (NZ) ........................................ 598443

(51) Int. Cl.
| | | |
|---|---|---|
| *A61K 31/00* | (2006.01) | |
| *A61K 9/00* | (2006.01) | |
| *A61K 47/00* | (2006.01) | |
| *A61K 31/546* | (2006.01) | |
| *A61K 47/02* | (2006.01) | |
| *A61K 47/14* | (2017.01) | |
| *A61K 47/26* | (2006.01) | |
| *A61K 9/10* | (2006.01) | |
| *A61K 45/06* | (2006.01) | |
| *A61K 31/7048* | (2006.01) | |
| *A61K 31/43* | (2006.01) | |
| *A61K 31/431* | (2006.01) | |
| *A61K 31/424* | (2006.01) | |
| *A61K 31/542* | (2006.01) | |
| *A61K 47/44* | (2017.01) | |

(52) U.S. Cl.
CPC .......... *A61K 31/546* (2013.01); *A61K 9/0041* (2013.01); *A61K 9/10* (2013.01); *A61K 31/424* (2013.01); *A61K 31/43* (2013.01); *A61K 31/431* (2013.01); *A61K 31/542* (2013.01); *A61K 31/7048* (2013.01); *A61K 45/06* (2013.01); *A61K 47/02* (2013.01); *A61K 47/14* (2013.01); *A61K 47/26* (2013.01); *A61K 47/44* (2013.01)

(58) Field of Classification Search
CPC .... A61K 31/43; A61K 31/546; A61K 31/424; A61K 9/0041; A61K 47/02; A61K 47/14; A61K 47/44
See application file for complete search history.

(56) References Cited

U.S. PATENT DOCUMENTS

| | | | |
|---|---|---|---|
| 3,234,086 A | 2/1966 | Hartman et al. | |
| 3,252,859 A * | 5/1966 | Silver .................. | A61K 9/0019 424/114 |
| 4,073,920 A | 2/1978 | Dowrick | |
| 4,282,202 A | 8/1981 | Dowrick | |
| 4,401,674 A | 8/1983 | Dowrick | |
| 4,980,175 A | 12/1990 | Chavkin et al. | |
| 5,122,377 A | 6/1992 | Miller et al. | |
| 6,369,040 B1 | 4/2002 | Acevedo et al. | |
| 6,787,342 B2 * | 9/2004 | Chen .................... | A61K 9/0014 435/183 |
| 7,812,009 B2 | 10/2010 | Cox et al. | |
| 7,842,791 B2 | 11/2010 | Britten et al. | |
| 2004/0033938 A1 * | 2/2004 | Britten ................. | A61K 9/0019 435/6.18 |
| 2006/0177506 A1 | 8/2006 | Yanai et al. | |
| 2008/0153894 A1 * | 6/2008 | Britten ................. | A61K 31/415 514/406 |
| 2009/0232899 A1 | 9/2009 | David et al. | |
| 2010/0261688 A1 | 10/2010 | Heep et al. | |
| 2011/0280853 A1 * | 11/2011 | Fallon .................... | A01N 63/02 424/94.2 |

(Continued)

FOREIGN PATENT DOCUMENTS

| | | |
|---|---|---|
| EP | 0058015 A2 | 8/1982 |
| EP | 0212875 A2 | 3/1987 |
| WO | 8703876 A1 | 7/1987 |

(Continued)

OTHER PUBLICATIONS

ICI Americas, Inc. "The HLB System: a time-saving guide to emulsifier selection", revised Mar. 1980, Wilmington, Delaware 19897.*
Hobza et al., J. Phys. Chem., 1981, vol. 85, pp. 4061-4067.*
Caesar & Loretz GmbH, Material Safety Data Sheet according to Regulation (EC) No. 1907/2006 (REACH), Miglyol 812, published on Sep. 13, 2011; Revised Nov. 16, 2015.
'Pharmacy' (for pharmacy class professional), edited by Cui Fu De, pp. 19 and 233-237, People's Health Publishing House, Feb. 2004, Version 5.—Discloses background art on the general use of surfactants and the relationship between different surfactants and HLB values.

(Continued)

*Primary Examiner* — Sikarl A Witherspoon
(74) *Attorney, Agent, or Firm* — McBee Moore & Vanik IP, LLC

(57) ABSTRACT

The present invention relates to a composition, the composition including a therapeutically effective amount of at least one active agent, and a base including, an amount of colloidal silica; at least one oil; and at least one surfactant, wherein the viscosity of the composition is below 1000 mPas at a shear rate of 100 1/s and at a temperature of 20° C.

26 Claims, 16 Drawing Sheets

(56) References Cited

U.S. PATENT DOCUMENTS

2011/0280854 A1* 11/2011 Fallon .................. A61K 38/465
424/94.2
2012/0129879 A1* 5/2012 Cantrell ............... A61K 9/0075
514/282

FOREIGN PATENT DOCUMENTS

| WO | 0001372 A2 | 1/2000 |
|---|---|---|
| WO | 0010528 A1 | 3/2000 |
| WO | 0160409 A1 | 8/2001 |
| WO | 03063877 A1 | 8/2003 |
| WO | 03070155 A2 | 8/2003 |
| WO | WO 03063877 A1 * | 8/2003 |
| WO | 2004057966 A1 | 7/2004 |
| WO | 2006008640 A1 | 1/2006 |
| WO | WO 2006008640 A1 * | 1/2006 |
| WO | 2006088305 A1 | 8/2006 |
| WO | 2011150481 A1 | 12/2011 |

OTHER PUBLICATIONS

Billany, M., 'Pharmaceutics, The Science of Dosage Form Design', Churchill Livingstone, London, 2002, Second Edition, ISBN 0-443-05517-3.

* cited by examiner

FIGURE 12

Example 1: WHP determined following ACVM guidelines

|  | MRL | 3 treatments / 24h | 6 treatments / 2 |
|---|---|---|---|
|  | Clox. | WHP | WHP |
|  | mg/L | h | h |
| NZ (EU) | 0.03 | 72 | 72 |

ACVM -
REGISTRATION STANDARD AND GUIDELINE FOR DETERMINATION OF A RESIDUE WITHHOLDING PERIOD FOR VETERINARY MEDICINES
ISBN 0-478-07709-2; 39 ACVM 03/03

FIGURE 14

|  | Treatment | Treatment period | WHP |
|---|---|---|---|
| NitroClox | 3x24h | 48h | 108h |
| Example 1 | 3x24h | 48h | 72h |

FIGURE 16

|  | Treatment | Treatment period | WHP |
|---|---|---|---|
| Orbenin LA | 3x48h | 96h | 84h |
| Orbenin LA | 5x24h | 96h | 96h |
| Example 1 | 6x24h | 120h | 72h |

CONTROLLED RELEASE COMPOSITIONS AND THEIR METHODS OF USE

TECHNICAL FIELD

This invention relates to controlled release compositions and their method of use, and preferably, but not specifically, to low viscosity controlled release compositions for the treatment of mastitis in lactating animals.

BACKGROUND ART

In order to treat lactating animals with mastitis or another microbial infection, antibiotic compositions are most often utilised. There are a number of commercially available antibiotic compositions used for intramammary mastitis treatment during the lactation period.

However, one of the major problems encountered with antibiotic treatments is a poor controlled release of the active agent over the treatment period. This can lead to problems with maintaining the active agent concentrations above the minimum inhibitory concentration wherein 90% of the microbes are killed (termed the MIC90). For instance, if the antibiotic is released too quickly, the antibiotic can come out with the first milking after administration. Then, the concentration of the antibiotic can be too low for the remaining period before receiving the subsequent administration, often 12 hours later. This can lead to failures in effectively treating the infection, longer treatment periods, and/or ultimately increased resistance against antibiotics.

To counter these problems, compositions such as Nitro-Clox™ (Long Acting) LA and Orbenin™ LA are often designed to have a higher viscosity, a known technique to slow the release profile of an active agent from a composition. Indeed, this is the approach taken for lactation and dry cow mastitis therapy known as long acting formulations, where the active is slowly released from a generally thick paste over an extended period of time. For instance, if the antibiotic gets administered 48 hourly during the lactation period, the antibiotic is released slowly with concentrations above MIC90 for about 36 hours after treatment. Then, the concentrations of the antibiotic are too low for the remaining period before receiving the subsequent administration, often 12 hours later. Again, this can lead to failures in effectively treating the infection.

Further reasons why chemists develop high viscosity compositions are because it can enhance the physical stability of the composition.

However, in the treatment of many conditions such as mastitis during the lactation period, a higher viscosity can lead to other problems. For example, high viscosity can lead to prolonged low levels of antibiotics in the milk and such milk must be withheld from the market. A long with-holding period (WHP) leads to lost revenue.

Also, a higher viscosity composition requires more force for infusion or injection of a formulation. This can lead to problems associated with increased difficulty with infusion (herein referred to as injectability) through a syringe to the udder.

For mastitis treatment, a higher viscosity of the composition can also lead to poorer distribution in the udder.

The need for thickeners or other excipients to increase viscosity of the compositions can also make the manufacturing process more time consuming and costly. Also, it is generally understood in the industry that the higher the viscosity of the composition, the more difficult it can be to handle during the manufacturing process.

A further problem that can be encountered with many suspensions used for mastitis treatment compositions is sedimentation of the suspension during storage. Of course, a higher viscosity of a composition can help to stabilise physically the suspension but a higher viscosity can not usually prevent sedimentation, it only slows the sedimentation. Consequently, even viscous suspensions will eventually sediment and the sediment may then cake, often proving difficult to re-disperse prior to administration. A high viscosity composition can hinder the re-dispersability of the sediments.

Therefore, there is a long felt need in the industry to develop improved compositions for the treatment of conditions such as mastitis during the lactating period of an animal. In the case of mastitis treatment, desired traits of such a composition may include:
  controllable release profile of the active agent;
  a short with-holding period (WHP)—for example, for treatment of conditions such as mastitis during the lactation period of the animal;
  good re-dispersability after storage, or before administration;
  ease of injectability or other mode of administration;
  good distribution of the composition into the region to be treated;
  the composition's base being adaptable to use with different active agents for treating or preventing any disease or condition, yet controlled and/or sustained release of the active;
  the composition's base being adaptable to account for different treatment regimes (i.e. different controlled release profiles); and/or
  easy to manufacture, and using pharmaceutically acceptable excipients.

It is an object of the present invention to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

Throughout this specification, the word "comprise", or variations thereof such as "comprises" or "comprising", will be understood to imply the inclusion of a stated element, integer or step, or group of elements integers or steps, but not the exclusion of any other element, integer or step, or group of elements, integers or steps.

Further aspects and advantages of the present invention will become apparent from the ensuing description which is given by way of example only.

DISCLOSURE OF INVENTION

According to one aspect of the present invention there is provided a composition,
the composition including a therapeutically effective amount of an active agent or active agents, and
a base including,
an amount of colloidal silica
at least one oil; and at least one surfactant,
wherein the viscosity of the composition is below 1000 mPas at a shear rate of 100 l/s and at a temperature of 20° C.

The inventors surprisingly found that the composition was particularly effective in the case of mastitis treatment as it may help to provide:
- a controllable release profile of the active agent, for instance which may be used to maintain active agent concentrations above MIC90 during the treatment period;
- a low viscosity to help with injectability, re-dispersability and/or good distribution in the udder, and/or
- a shorter WHP compared to other currently available mastitis compositions.

As will be discussed further, the inventors have recognised the particular importance of this invention to antibiotic treatment of mastitis. However, it would be reasonably expected by someone skilled in the art that the same inventive concept of the disclosed composition would apply to a controllable release profile of substantially any active agent or compound in need thereof for treatment of other conditions.

Without wishing to being limited to a mode of action, it is believed that this controllable release may be due to the surfactant interacting with the colloidal silica, with the result being a change in the release profile of the active agent from the composition.

Importantly this control of the release profile of the active agent may be achieved without overly altering the viscosity of the composition, and in particular without a substantial increase in the composition's viscosity.

By example in FIG. 2, in vitro studies showed the inventors were able to decrease drug recovery (equating to a decreased release profile in vivo) in dissolution media from approximately 50% to 5% w/w over a 180 minute time period. This beneficial effect was obtainable while the viscosity of the composition only increased marginally from 90 mPas to 118 mPas (at a shear rate of 100 l/s at a temperature of 20° C.). As shown in FIG. 2, this recovery rate of 5% w/w was similar to that obtained by a competing product, Orbenin™ LA. However, Orbenin™ LA has a viscosity of 1080 mPas, approximately 10 fold of that seen in this example in the present invention.

Obviously, if the need arises for a higher viscosity composition, this can be achieved by using thickeners as well known in the art.

For example, when treating mastitis during the lactation period, a lower viscosity composition may be achieved which helps to provide numerous advantageous features such as easy re-dispersability, injectability, manufacturing and/or a shorter WHP. Such features may be provided whilst altering the release profile of the composition's active agent to suit the requirements desired. In the treatment of mastitis for example, this controlled release may be used to ensure the active agent is kept above the MIC90 during the entire treatment period.

The inventors have conducted preliminary trials as exemplified herein which illustrates the significant advantages.

PREFERRED EMBODIMENTS OF THE COMPOSITION

Active Agent

Preferably, the active agent is an antibiotic, a combination of antibiotics or an antibiotic combined with a non-antibiotic active agent. The inventors acknowledge a preferred antibiotic is cloxacillin due to its effectiveness in treating mastitis. Preferably, the cloxacillin is given as cloxacillin sodium. Of course, other forms of cloxacillin, such as cloxacillin benzathine, may also be used.

Other preferred active agents include beta-lactams, penicillins, cephalosporins, aminoglycosides, quinolones, fosfomycin, sulphonamides, tetracyclines and macrolide antibiotics.

Preferred combinations of active agents include amoxicillin and clavulanic acid; penicillin active agent and aminoglycoside; cloxacillin and tylosin; and an antibiotic and a non-steroidal anti-inflammatory drug.

However, substantially any antibiotic, non-antibiotic active agent, or functional derivatives thereof may be utilised in the present invention.

For example, the inventors have exemplified that the invention also works in a similar fashion when the active agent is a tylosin base, cephapirin sodium or cephapirin benzathine antibiotic.

It was also surprising to find that the release rate can be affected depending on the type of active agent used. When the type/amount of silica and surfactant is kept constant, altering the active agent from cephapirin and cloxacillin (both kept at a concentration of approximately 4.5% w/w) resulted in a very different release rate. Cephapirin was released much slower than cloxacillin. This illustrates that by adjusting the type and possibly the concentration of active agent (and if appropriate the silica and surfactant), a desired release of substantially any active agent may be achieved.

Preferably, the active agent is micronised. The term micronised should be taken as meaning a particle with a mass mean diameter d50 between to 1-20 μm Micronisation helps to reduce sedimentation velocity. Furthermore, larger particles may form bridges in front of the syringe nozzle which may affect syringeability. Throughout this specification, the term injectability or syringeability should be taken as meaning the ease of administering the medicament to the animal through a syringe. This is typically affected by viscosity, as well as the particle size of the drugs or formulation excipients, which can sometimes partially or fully block the tip of the syringe path during administration of the medicament.

Colloidal Silica

Throughout this specification the term colloidal silica should be taken as meaning particles of fumed amorphous silica with a greatest diameter of a single silica particle between approximately 1 nm and 1000 nm (1 μm).

A further discussion on the known traits and uses of colloidal silica is provided later in this specification. This helps to illustrate that the present use of colloidal silica is very different to the previously known uses as a thickening and/or anti-caking agent.

Preferably, the colloidal silica is fumed colloidal silicon dioxide.

Many different types of fumed colloidal silica are currently available. A person skilled in the art would appreciate that all currently available and future types of fumed colloidal silica would provide the same advantages as discussed herein. As exemplified in this specification, fumed colloidal silicon dioxide was found to be particularly effective.

Preferably, the fumed colloidal silica has hydrophobic properties.

The inventors identified hydrophobic colloidal silica may be significantly more effective than hydrophilic colloidal silica at altering the release profile of the active agent, whilst keeping the viscosity relatively low and/or substantially unchanged. This was a surprising result as formulations using hydrophobic colloidal silica have a lower viscosity than those using its hydrophilic counter-part. Hydrophilic colloidal silica is known to be used as a thickening agent, which imparts a slower release profile as result of the thickened composition.

Instead, when the inventors used hydrophilic silica, inclusion of a surfactant tended to increase the viscosity of the composition more than when compared to using hydrophobic silica. This was a particularly surprising result, as the use of hydrophobic silica instead of hydrophilic silica in the present invention tended to provide a greater control of the active agent's release.

A preferred commercially available hydrophobic colloidal silicon dioxide is Aerosil® R972 (supplied by Aerosil).

Preferably, the concentration of colloidal silica is between 0.1-5% w/w. This amount was found to be particularly effective when used in a treatment of mastitis during the lactation period, as per the preferred dosage regimes discussed herein.

More preferably, the concentration of colloidal silica is between 1-3% w/w. A particularly preferred amount of colloidal silica was in the order of 1.75% w/w. For example, this was found to allow suitable release of the active over the treatment period (typically 24 hours) to maintain the cloxacillin above the MIC90, yet simultaneously provided a beneficially shorter WHP than competing reference products. This is just one example of how the controlled release mechanism of the present invention may be effectively utilised.

As discussed above, the amount of colloidal silica used may be governed partially by the type of active used, and the desired release rate. For example, cephapirin is shown to release considerably slower from the base of the composition than cloxacillin.

For this reason, one may decide to lower the amount of colloidal silica to achieve a similar release rate to that provided when using cloxacillin if so desired.

In-vivo protocols are well known in the industry and provide a straightforward test to determine the resulting active agent concentration in milk from a given composition. From such studies, a person skilled in the art would be able to easily adjust the amount of colloidal silica (or for that matter the active, or amount/type of surfactant) to achieve the desired release rate of substantially any composition.

Overall, it was found by the inventors that the higher the concentration of colloidal silica in the base of the composition, the slower the release rate of the active agent. Importantly, this slowed release rate may be achieved without overly affecting the viscosity of the compositions. In competing compositions, such as NitroClox™ LA or Orbenin™ LA, a similar release rate can only be achieved through a much higher viscosity, which has numerous disadvantages as discussed.

Surfactant

Throughout this specification the term surfactant should be taken as meaning any compound that lowers the surface tension of a liquid, any compound that lowers the interfacial tension between two liquids, or any compound that lowers the interfacial tension between a liquid and a solid. Surfactants may also act as emulsifiers, detergents, wetting agents and so forth.

Preferably, the surfactant is a non-ionic surfactant.

However, the inventors consider amphoteric, anionic or cationic surfactants should work as well.

Preferably, the non-ionic surfactant has a hydrophilic-lipophilic balance (HLB) range between 0.5 and 30.

More preferably, the non-ionic surfactant has a HLB range between 4 and 16.

More preferably, the surfactant is chosen from the group selected from sorbitan esters, polyoxyethylene sorbitan fatty acid esters, polyoxyethylene castor oil derivatives, polyoxyethylene stearates, and polyethylene oxide monooleate, and combinations thereof.

Surprisingly, some surfactants appeared to work better than others at controlling a chosen active agent's release rate.

For example, 0.1% w/w PEG12-oleate had a greater effect at slowing the release rate of cloxacillin than 0.1% w/w Span 80, while all other variables were kept constant.

Preferably, the surfactant is at a concentration between 0.01 to 10% w/w.

The inventors found that the more surfactant in the base of the composition, the slower the release rate of the active agent.

For this reason, the amount/type of the surfactant and/or the ratio of surfactant to colloidal silica may provide a means to control the release rate of the active agent.

Preferably, the ratio of colloidal silica to surfactant is between 1:100 and 500:1.

Most preferably, the ratio of colloidal silica to surfactant is between 1:5 and 6:1.

Optionally, the base may include more than one type of surfactant. It would be reasonable to expect that the resulting composition's release profile (and other characteristics such as WHP) may be more finely controlled by using a combination of surfactants in a single composition, and/or in different compositions administered during the course of treatment.

Oil

In many compositions, oils are needed as a vehicle. For example, antibiotic compositions including actives such as cloxacillin or cephapirin are typically based on an oily vehicle. For example, this helps the composition to be administered as an infusion through the teat canal or an injection and/or achieving sufficient chemical stability during its shelf life.

Preferably, the oil has a low viscosity.

The use of a low viscosity oil helps to ensure the resulting composition retains a low viscosity. This may help ensure the composition has good distribution within the udder, is easy to re-disperse after storage, and is easy to administer through a syringe.

Preferably, the viscosity of the oil is between 1 and 100 mPas at 20° C.

More preferably, the viscosity of the oil is less than 40 mPas at 20° C.

More preferably, the oil is selected from the group consisting of medium chain triglycerides (eg Miglyol 812 or Miglyol 840), ethyl oleate, light liquid paraffin, sesame oil and peanut oil. However, it should be appreciated that other similar low viscosity oils may be utilised for the present invention.

Preferably, the oil has a low density between 0.80 and 0.99 g/cm$^3$.

As exemplified in FIG. 6, the inventors found that different oils used altered the recovery rate of the active agent. The effect was not as pronounced when compared to alterations in the type/amount of surfactant, colloidal silica or active agent used. Therefore, it is possible such changes may be due simply to the viscosity of the oil, and that of the resulting composition. Therefore, in a preferred embodiment, a lower viscosity oil is used to maintain a lower viscosity of the composition.

Yet, the inventors also consider that the oil may be interacting with one or more of the components in the base of the composition to affect the recovery rate of the active agent in a separate manner to just viscosity-related controlled release.

Viscosity of the Final Composition

Obviously, the viscosity of the composition may be tailored to the specific requirements needed. For some compositions, a relatively high viscosity may be used. In others, a low viscosity may be maintained by not adding excipients such as thickeners or high viscosity oils. Such viscosity modifiers may also contribute, if necessary, to the release profile of the active.

The preferred viscosity ranges and values discussed below are those which the inventors have found to be particularly beneficial for the intramammary treatment of mastitis during the lactation period.

Unless specified otherwise, viscosities of the composition referred to within this specification are based on measurements using a concentric cylinder method at a shear rate of 100 l/s and at a temperature of 20° C. The viscosity of the compositions according to the present invention are below 1000 mPas when measured at these conditions.

More preferably, the final composition has a viscosity below 300 mPas.

Most preferably, the composition has a viscosity below 150 mPas.

NitroClox™ LA and Orbenin™ LA have a viscosity above 1000 mPas at a shear rate of 100 1/s and a temperature of 20° C. Similarly, dry cow mastitis treatments or other compositions which include colloidal silica typically have a viscosity well above this upper limit.

The inventors identified that a composition for the treatment of mastitis during the lactation period preferably has a viscosity below 1000 mPas (and more preferably below 300 mPas) may provide better characteristics in terms of good syringeability, re-dispersability, udder distribution and/or short WHP when compared to competing compositions such as NitroClox™ LA and Orbenin™ LA. These beneficial features may be retained whilst ensuring the release profile of the active is suitably controlled to allow the active to maintain substantially above the MIC90 during the entire treatment period.

Preferred Method of Treatment

Preferably, the composition described herein is used to treat mastitis as an intramammary infusion during the lactation period.

In the case of mastitis arising during the lactation period, the composition may be used in bovine, ovine or other animals typically used for commercial milk production.

This helps to differentiate the preferred use of the present invention from dry period mastitis treatment (i.e. treatment outside the lactation period).

Yet, it is clear that the present invention may be used to treat substantially any condition or disease depending on the active agent selected. The underlying inventive concept of the composition should not be limited to compositions for intramammary treatment of mastitis.

According to a further aspect of the present invention there is provided a method of treating a microbial infection in an animal in need thereof with a composition as substantially described herein wherein the method includes the step of administering the composition by intramammary infusion.

The method of administering the composition may typically be through infusion through the teat canal.

Preferably, the method includes a dosage regime of between 1-12 doses of 1-10 g composition with a treatment regime of administration every 12, 24 or 48 hours.

More preferably, the method includes a dosage regime of 3 or 6 doses of 5 g composition with a treatment regime of 24 hours over a treatment period of 48 hours (3 doses) to 120 hours (6 doses).

This dosage regime may be sufficient to successfully treat an animal with pre-clinical or clinical mastitis during the lactation period.

After the calculated WHP, normal milking production can resume again. Again, the inventors found the WHP of the present invention may be substantially lower than other currently available formulations, such as NitroClox™ LA when the same treatment periods were compared.

FIG. 14 exemplifies one composition of the present invention having a WHP of 72 hours compared to NitroClox™ LA with a WHP of 108 hours (treatment regime three doses at 24 h intervals). Based on the assumptions in the paragraph below, this would equate to an increased profit of $24 per cow due to a 36 hour shorter WHP. When this is multiplied over a large dairy farm, or indeed an entire nation, one can easily see the importance of this invention.

The increased profit of $24 per cow assumes what is generally understood in the New Zealand dairy industry, as outlined below. Each milking typically provides approximately 10 L of milk (equalling 1 kg of milk solids), and a farmer sells 1 kg of milk solids for $8 to a company such as Fonterra. Furthermore, each cow will typically be milked every 12 hours.

A particularly advantageous use of the present invention may be the combination treatments of different compositions having different release profiles during the treatment period.

To illustrate this, a mastitis treatment may encompass the initial use of a relatively slow active-releasing composition over the first part of the treatment period, yet the latter treatment(s) may use a faster active-releasing composition.

This may help in the sense that fewer treatments may be required towards the beginning of the treatment period. It may also help to ensure the active is kept above the MIC90. Towards the end of the treatment period, a faster releasing composition may be used essentially to top up the active agent levels. Yet, because the active is released faster, the WHP period may still be kept shorter.

Preferred Method of Manufacture

According to a further aspect of the present invention there is provided a method of manufacturing the composition as substantially described above including the steps of:

a) mixing the oil and surfactant in a container to form a homogenous oil mixture;
b) dispersing the active agent in the oil mixture; and
c) subsequently adding the colloidal silica to the oil mixture.

Optionally, at least one preservative is mixed in with the oil and surfactant in step a). For example, methyl paraben and propyl paraben may be used as preservatives.

Preferably, the oil mixture formed from step a) is heat sterilised. For example, the inventors utilise a three hour incubation at 140° C., and then subsequently allow the mixture to cool.

Preferably, step b) and step c) utilise high shear dispersion equipment.

Preferably, the colloidal silica in step c) is also heat sterilised before being added to the oil mixture.

Preferably, the oil mixture formed after step c) is homogenously mixed.

The inventors identified that the composition's preferred low viscosity also helps with the manufacturing process. Unlike other compositions, there is no extra heating step required to mix in a thickener (e.g. hydroxystearin).

Also, the lower viscosity may help when syringes need to be filled after manufacturing the composition and prior to administration.

The preferred use of micronised active agents also helps to prevent quick settling of the composition. Additionally, the inventors consider it possible that the release of a micronised active is easier to control than non-micronised equivalents, potentially because the particle size distribution is likely more consistent. Also, it is possible that any interaction with other components from within the composition is likely to be enhanced with the larger surface area of the smaller micronised particles.

Additional Background of Colloidal Silica

Fumed colloidal silica, such as colloidal silicon dioxide, is typically used as viscosity modifiers, and more particularly, thickening agents in liquid formulations. Some examples of how colloidal silica has been used follows. In line with what was commonly understood in the art, colloidal silica was known to aid in altering the release of actives from a composition, but only in the sense of it acting as a thickener. As discussed before, generally the thicker a composition becomes, the slower the release profile of the active is, and vice versa. This is an entirely different concept from the present invention.

NZ523128 discloses a veterinary drench product including an active dissolved in a solvent then adsorbed on a sorbing medium such as Aerosil R972 fumed silica, then dispersing the solvent into another liquid that contains another active dissolved or suspended therein.

WO 03070155 discloses a formulation for oral administration including an active agent suspended in an oily matrix, with surfactant and colloidal silicon dioxide. The composition is made into a viscous solution with the addition of hydrogenated vegetable oil, including yellow beeswax as a suspending agent, lecithin. Silicon dioxide is used as a dispersion aid and pseudoephedrine HCl, for use in a gelatin capsule.

WO0160409 discloses a paste formulation including an active agent, fumed silica, a viscosity modifier, an absorbent, a colourant, and a carrier. The viscosity modifier includes PEG 200-600, monoethylamine, glycerol, and propylene glycol.

WO9824436 discloses a gel formulation including colloidal silicon dioxide and triacetin.

JP 3153623 (based on English translation of Abstract) discloses a semisolid pharmaceutical composition for oral administration. The composition includes a drug, a physiologically permissible liquid, an edible oil, a colloidal silicon dioxide, aluminum stearate or a high-molecular weight polyethylene glycol.

U.S. Pat. No. 4,980,175 discloses a liquid compositions for oral administration, including antacid ingredient (aluminium hydroxide etc.) and colloidal silicon dioxide suspended in medium chain triglycerides. An emulsifier (hexaglycerol monoleate) is included to reduce the taste of the oil.

U.S. Pat. No. 4,781,920 discloses an anthelmintic paste including mineral oil, polysorbate 20 surfactant, fumed silica and tetramisole resinate.

These documents do not disclose that the combination of the components (and in particular the surfactant and the colloidal silica) would interact to provide a controlled release mechanism of the active agent. Furthermore, those that do include both surfactant and a colloidal silica are described as viscous liquid compositions or pastes which would not fall within the scope of the present invention (a composition with a viscosity below 1000 mPas). The colloidal silica used in such compositions are typically used as viscosity modifiers (thickeners) to directly impart a controlled release.

In other instances, fumed colloidal silica is used for tablet or powder formulations as a free-flow agent. AEROSIL discusses other typical applications of colloidal silica on their website, such as anti-caking and a stabiliser.

Fumed colloidal silica exists in particles (termed primary, secondary or tertiary particles depending on their level of aggregation and/or agglomeration).

Under mechanical stress, the silica tertiary structure is broken down to primary or secondary aggregates, the system becomes more fluid, and the viscosity drops. Once returning to rest, the tertiary structure of agglomerated silica particles builds up again, and the viscosity returns to its original value.

As stated in the Technical Information 1279, Aerosil, Degussa, hydrophobic AEROSIL® ("R") grades have been treated during manufacture to obtain a hydrophobic surface. During this process, silanol groups are reacted. Interestingly, hydrophobic AEROSIL® types often exhibit lower thickening efficiency compared to hydrophilic types.

Therefore for liquid dosage forms, hydrophilic fumed silica is recommended for viscosity control and therefore slower active agent release and hydrophobic fumed silica is recommended for stabilisation to prevent hard sediments (i.e. caking) from forming, particularly during storage.

The general principle as employed in formulation chemistry is: an increase of thickening agent concentration in a formulation, the greater the viscosity, and the slower the active agent release from the resulting formulation.

Therefore it was surprising to find that altering the components of the present composition substantially influences the release profile of the active agent without overly affecting the viscosity. This is clearly exemplified the examples provided in this specification.

As exemplified in FIG. 10, cloxacillin release from a preferred composition can be finely controlled and extended with concentrations in milk above MIC90=0.5 mg/L (for Cloxacillin in New Zealand, number taken from Salomon et al, 1998 J Dairy Sci 81:570-578) for more than 48 hours after treatment (example 17). This can not be achieved with current products in the market with a treatment regime of 48 hours, such as NitroClox™ LA (FIG. 13) and Orbenin™ LA (FIG. 15) even though the viscosity is much higher in comparison.

Colloidal silica has been employed in the Orbenin™ LA formulation manufactured by Pfizer, yet only for conventional uses, such as a thickener and/or anti-caking agent. A further thickener, hydroxystearin, is added with the colloidal silica to increase the formulation's viscosity which is used to achieve a slow release of the active agent. There is no inclusion of a surfactant in the Orbenin™ LA formulation, unlike the present invention.

As a result of the thickener used in the Orbenin™ LA composition, it has a much higher viscosity than that achieved by the present invention (as outlined in the examples). As previously discussed, this can lead to problems with injectability. Therefore, the inventors consider the present invention, which is able to achieve a lower viscosity whilst being able to control active agent release effectively, has significant advantages over Orbenin™ LA.

WO 87/03876 also discloses a treatment/prevention formulation for mastitis during the dry period. WO 87/03876 discusses the use of colloidal silica together with the addition of further thickeners in order to provide a viscous formulation. Again, the result of this highly viscous formulation is to provide a controlled release of the active over a longer treatment period (during the dry period opposed to lactating period). This is different to the use of colloidal silica in the present invention.

WO 03/063877 also discloses the use of colloidal silica for mastitis treatment during the dry period. Again, the aim is to provide a high viscosity formulation using colloidal silica as a thickener for slow release of the antibiotic.

U.S. Pat. No. 4,401,674 discloses an intramammary formulation containing penicillin and a molecular sieve. Colloidal silica is different to molecular sieves. Molecular sieves are typically a few microns (μm) in diameter making them considerably larger than colloidal silica particles. Unlike colloidal silica, molecular sieves do not have thickening properties and, as such, are not typically used as thickening agents.

Column 1, line 54 to 58 of U.S. Pat. No. 4,401,674 discusses that if the formulation is to be used for lactating cows, an emulsifying agent (or alternatively a coconut oil) may be added into the composition to "hasten the mixing of the composition with the aqueous secretions in the udder." This is quite different to the concept of the present invention, where the surfactant appears to be chemically interacting with the silica structure to impart a change in the release rate. For example, the release rate of the active agent is slowed down with increasing surfactant concentration. Depending on the type/amount of surfactant, silica and/or active agent, the release rate of the active agent from the composition may be altered, and importantly without overly affecting viscosity.

Also, U.S. Pat. No. 4,401,674 does not disclose or teach that an emulsifying agent would alter the release rate of the active agent. It merely is provided to hasten the mixing of the composition.

BRIEF DESCRIPTION OF DRAWINGS

Further aspects of the present invention will become apparent from the ensuing description which is given by way of example only and with reference to the accompanying drawings in which:

FIG. 12 WHP determination of Example 1 composition based on ACVM guidelines (in vivo)

FIG. 14 Comparison of WHP between Example 1 composition and NitroClox™ LA (in vivo)

FIG. 16 Comparison of WHP between Example 1 composition and Orbenin™ LA (in vivo)

BEST MODES FOR CARRYING OUT THE INVENTION

Part 1: Example Compositions

Figure 1:
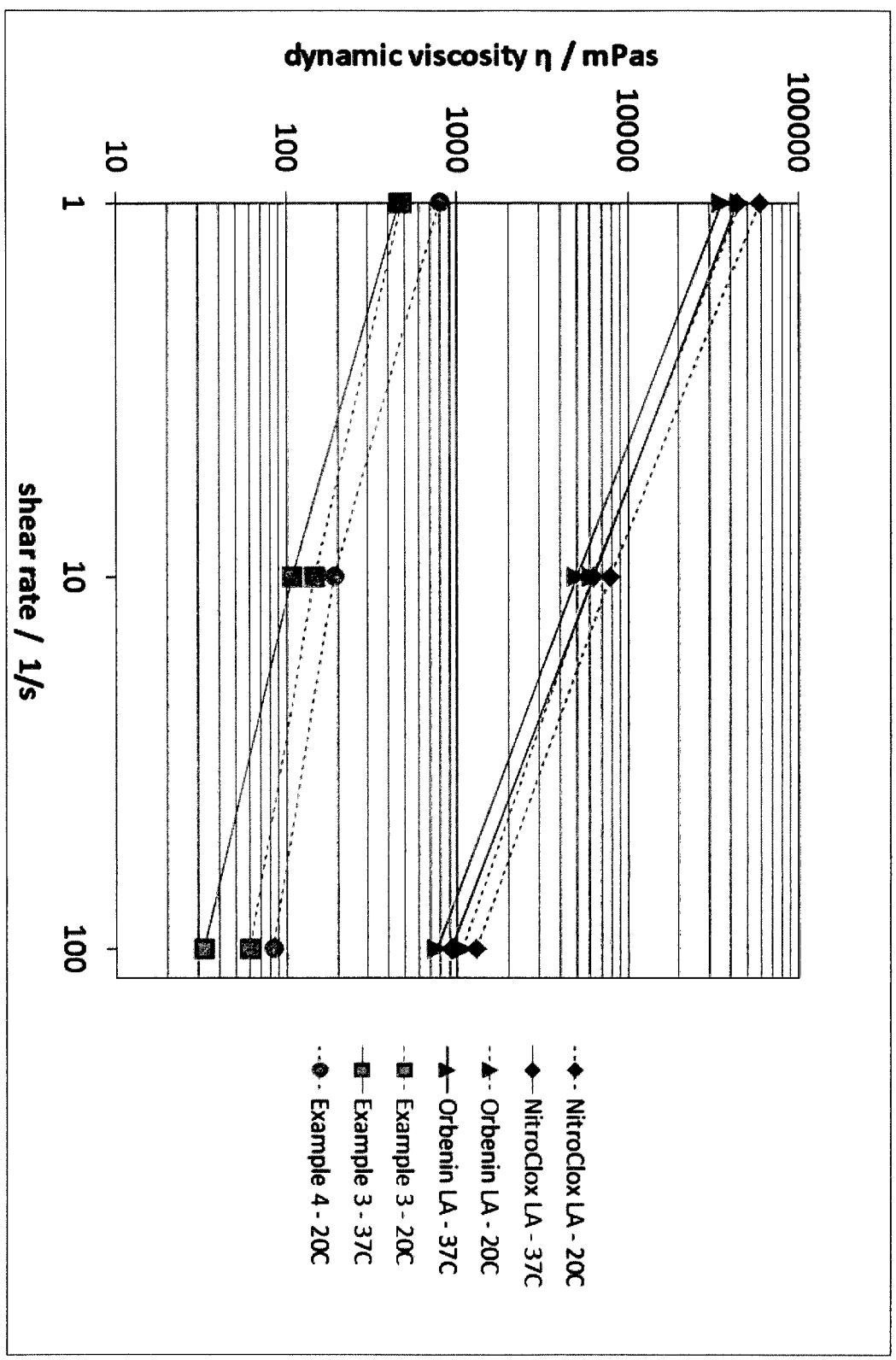
FIG. 1 Comparison of dynamic viscosities between mastitis treatment compositions (lactation period treatment)

| Example 1 | | |
|---|---|---|
| | mg | w/w-% |
| Cloxacillin sodium | 231 | 4.62% |
| Methyl paraben | 3.75 | 0.075% |
| Propyl paraben | 1.25 | 0.025% |
| Aerosil R972 Pharma | 87.5 | 1.75% |
| Span 80 | 25 | 0.50% |
| Miglyol 812 | 4651.5 | 93.03% |
| Total | 5000 | 100.00% |

| Example 2 | | |
|---|---|---|
| | mg | w/w-% |
| Cephapirin sodium | 220.9 | 4.42% |
| Methyl paraben | 3.75 | 0.075% |
| Propyl paraben | 1.25 | 0.025% |
| Aerosil R972 Pharma | 87.5 | 1.75% |
| Span 80 | 25 | 0.50% |
| Miglyol 812 | 4651.5 | 93.03% |
| Total | 5000 | 100.00% |

| Example 3 | | |
|---|---|---|
| | mg | w/w-% |
| Cloxacillin sodium | 231 | 4.62% |
| Aerosil R972 Pharma | 100 | 2.00% |
| Span 80 | 25 | 0.50% |
| Miglyol 812 | 4644 | 92.88% |
| Total | 5000 | 100.00% |

| Example 4 | | |
|---|---|---|
| | mg | w/w-% |
| Cloxacillin sodium | 231 | 4.62% |
| Aerosil R972 Pharma | 150 | 3.00% |
| Span 80 | 100 | 2.00% |
| Miglyol 812 | 4519 | 90.38% |
| Total | 5000 | 100.00% |

Example 5

|  | mg | w/w-% |
|---|---|---|
| Cloxacillin sodium | 459 | 9.18% |
| Aerosil R972 Pharma | 87.5 | 1.75% |
| Span 80 | 100 | 2.00% |
| Miglyol 812 | 4354 | 87.07% |
| Total | 5000 | 100.00% |

Example 6

|  | mg | w/w-% |
|---|---|---|
| Cloxacillin sodium | 459 | 9.18% |
| Aerosil R972 Pharma | 112.5 | 2.25% |
| PEG12Oleate | 5 | 0.10% |
| Miglyol 812 | 4423.5 | 88.47% |
| Total | 5000 | 100.00% |

Example 7

|  | mg | w/w-% |
|---|---|---|
| Cloxacillin sodium | 459 | 9.18% |
| Aerosil R972 Pharma | 112.5 | 2.25% |
| PEG12Oleate | 2.5 | 0.05% |
| Miglyol 812 | 4426 | 88.52% |
| Total | 5000 | 100.00% |

Example 8

|  | mg | w/w-% |
|---|---|---|
| Cloxacillin sodium | 459 | 9.18% |
| Aerosil R972 Pharma | 112.5 | 2.25% |
| Span 80 | 2.5 | 0.05% |
| Miglyol 812 | 4426 | 88.52% |
| Total | 5000 | 100.00% |

Example 9

|  | mg | w/w-% |
|---|---|---|
| Cloxacillin sodium | 459 | 9.18% |
| Aerosil R972 Pharma | 112.5 | 2.25% |
| Span 80 | 5 | 0.10% |
| Miglyol 812 | 4423.5 | 88.47% |
| Total | 5000 | 100.00% |

Example 10

|  | mg | w/w-% |
|---|---|---|
| Cloxacillin sodium | 459 | 9.18% |
| Aerosil R972 Pharma | 112.5 | 2.25% |
| Span 80 | 25 | 0.50% |
| Miglyol 812 | 4403.5 | 88.07% |
| Total | 5000 | 100.00% |

Example 11

|  | mg | w/w-% |
|---|---|---|
| Cloxacillin sodium | 459 | 9.18% |
| Aerosil R972 Pharma | 112.5 | 2.25% |
| Span 80 | 50 | 1.00% |
| Miglyol 812 | 4378.5 | 87.57% |
| Total | 5000 | 100.00% |

Example 12

|  | mg | w/w-% |
|---|---|---|
| Cloxacillin sodium | 459 | 9.18% |
| Aerosil R972 Pharma | 112.5 | 2.25% |
| Span 80 | 100 | 2.00% |
| Miglyol 812 | 4328.5 | 86.57% |
| Total | 5000 | 100.00% |

Example 13

|  | mg | w/w-% |
|---|---|---|
| Cloxacillin sodium | 459 | 9.18% |
| Aerosil R972 Pharma | 150 | 3.00% |
| Span 80 | 100 | 2.00% |
| Miglyol 812 | 4291 | 85.82% |
| Total | 5000 | 100.00% |

Example 14

|  | mg | w/w-% |
|---|---|---|
| Cloxacillin sodium | 459 | 9.18% |
| Aerosil 200 Pharma | 150 | 3.00% |
| Span 80 | 100 | 2.00% |
| Miglyol 812 | 4291 | 85.82% |
| Total | 5000 | 100.00% |

Example 15

|  | mg | w/w-% |
|---|---|---|
| Cloxacillin sodium | 459 | 9.18% |
| Aerosil R972 Pharma | 150 | 3.00% |
| Span 80 | 100 | 2.00% |
| Peanut Oil | 4291 | 85.82% |
| Total | 5000 | 100.00% |

Example 16

|  | mg | w/w-% |
| --- | --- | --- |
| Cloxacillin sodium | 200 | 2.00% |
| Tylosin base | 250 | 2.50% |
| Aerosil R972 Pharma | 400 | 4.00% |
| Span 80 | 200 | 2.00% |
| Methyl paraben | 0.4 | 0.004% |
| Propyl paraben | 0.2 | 0.002% |
| Miglyol 812 | 8949.4 | 89.49% |
| Total | 10000 | 100.00% |

Example 17

|  | mg | w/w-% |
| --- | --- | --- |
| Cloxacillin sodium | 437 | 8.74% |
| Aerosil R972 Pharma | 150 | 3.00% |
| Span 80 | 100 | 2.00% |
| Methyl paraben | 0.4 | 0.008% |
| Propyl paraben | 0.2 | 0.004% |
| Miglyol 812 | 4312.4 | 86.25% |
| Total | 5000 | 100.00% |

Note that the cloxacillin sodium used in Examples 1-17 (and also Example 18 shown below) are in a micronised form.

Part 2: Exemplification of Controlled Release Rate of Active Agent

FIG. 1 illustrates the comparatively low viscosity of the preferred composition of the present invention compared to reference products currently on the market. Recovery rates in dissolution media (shown in FIGS. 2-6) are considered by the inventors to be indicative of in vivo release rates.

Figure 2:
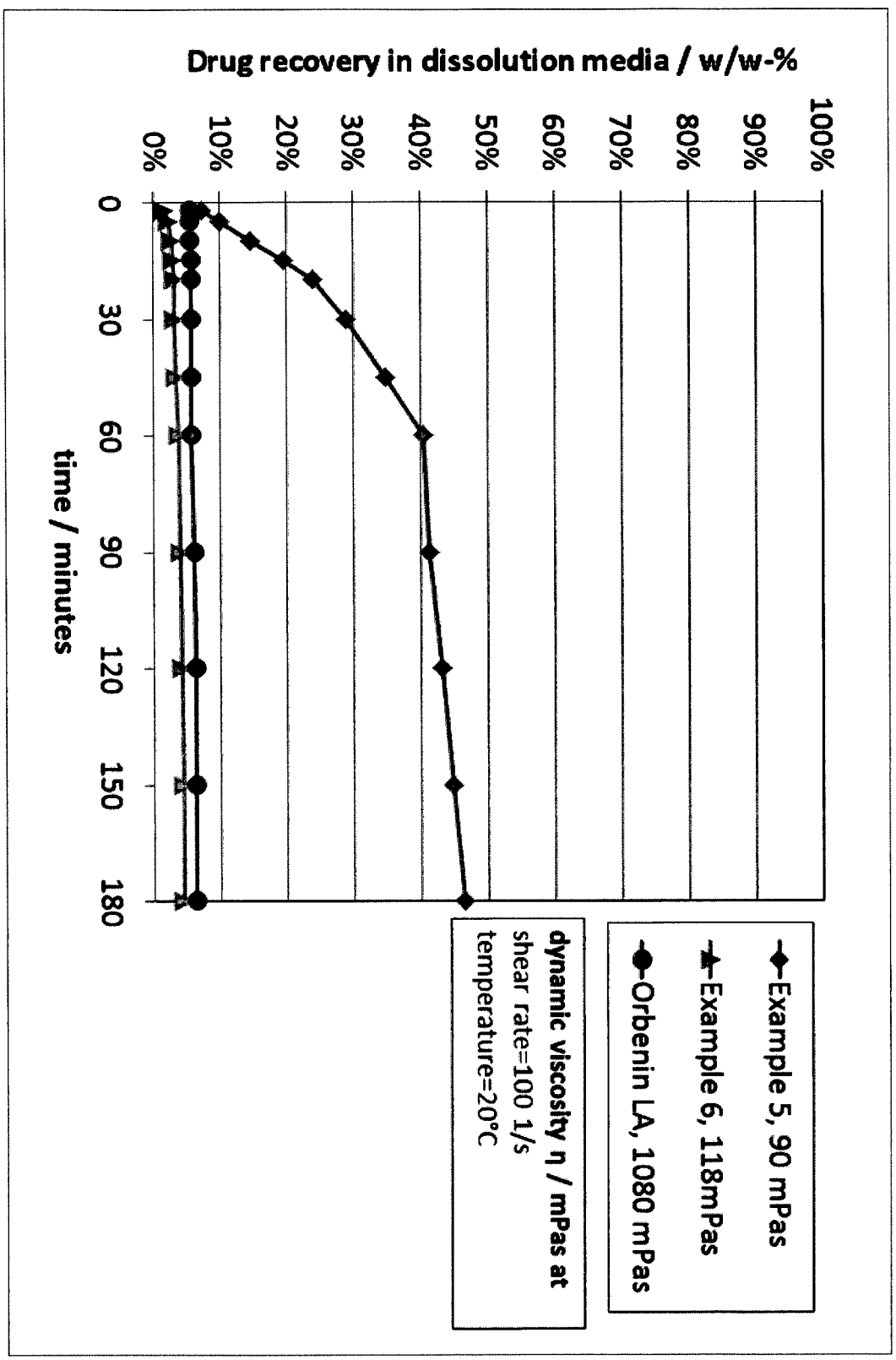
FIG. 2 Influence of surfactant on active agent recovery rate (in vitro)

FIG. 2 clearly illustrates one of the major advantages of the present invention. Compared to Orbenin™ LA, the two test compositions in FIG. 2 have very low viscosity (90-150 mPas vs 1080 mPas). Orbenin™ LA is able to maintain a relatively slow cloxacillin release (approximately 5%) by using a thickener (hydroxystearin). This viscosity of Orbenin™ LA compared to the current compositions can be visualised in FIG. 1.

The two test compositions depicted in FIG. 2 do not include a thickener to impart a slow recovery profile. Instead, careful selection of the surfactant (Span80 vs. PEG12-oleate) can be used to significantly alter the recovery profile of the cloxacillin without a significant rise in the viscosity. The test composition containing PEG12-oleate has a recovery profile substantially identical (if not slower) than Orbenin™ LA, yet the viscosity beneficially remains relatively low (180 mPas).

Figure 3:
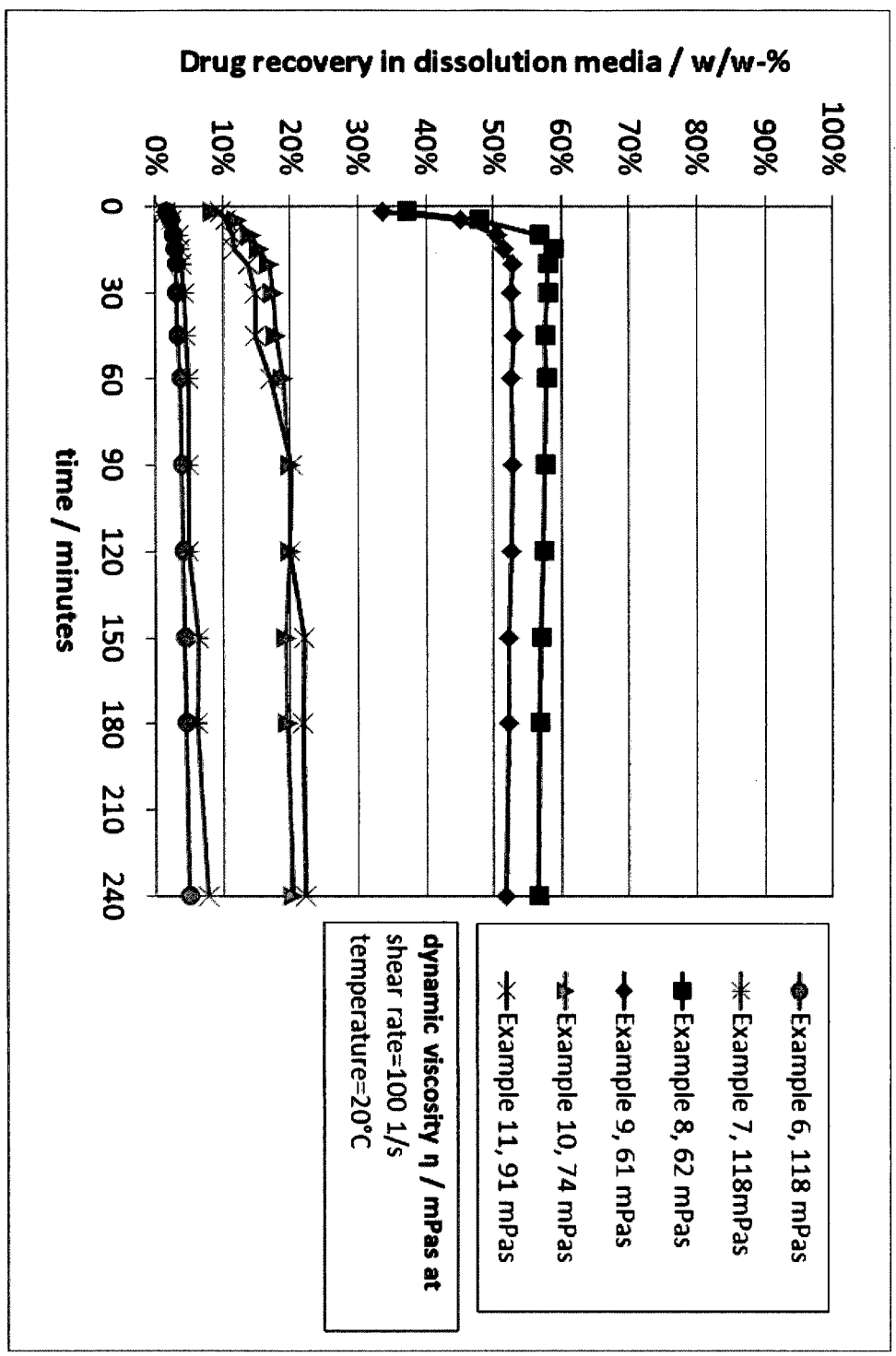
FIG. 3 Influence of surfactant on active agent recovery rate (in vitro)

FIG. 3 illustrates that the recovery rate of the active agent can be affected not only by the choice of the surfactant type, but also the concentration thereof. This is exemplified by the increase of the concentration of Span80 (HLB=4.3) from 0.05% to 1% (Examples 8 to 11). Only a small rise in the viscosity is seen, yet a disproportionate decrease in the active recovery is provided.

Similarly, alteration of the concentration of PEG12-Oleate (HLB=13.7) (Examples 6 and 7) is shown, with corresponding changes in the recovery profile. Therefore, this illustrates that different types and concentrations of surfactants may be used to control the release profile of compositions in vivo.

Figure 4:
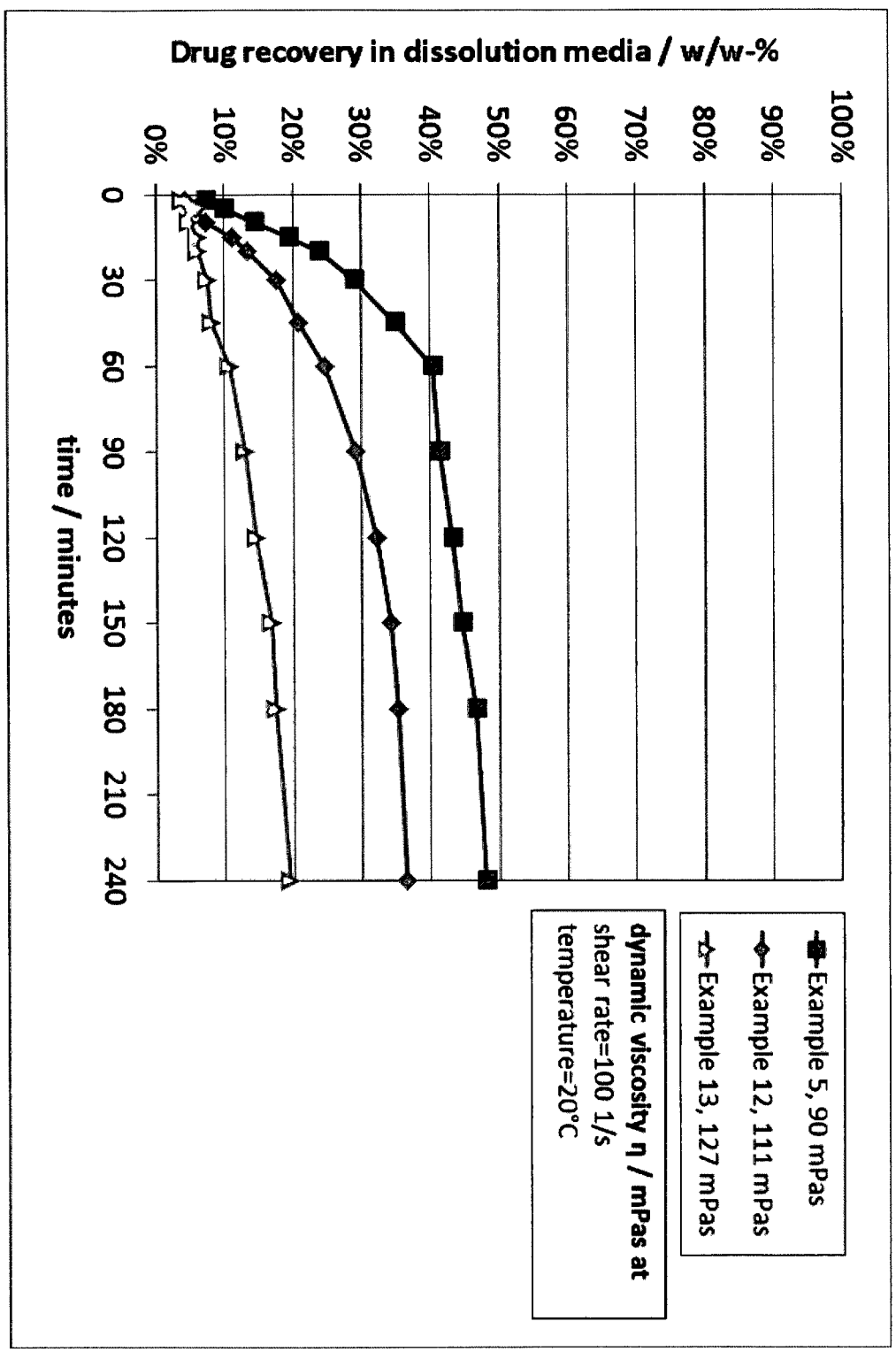
FIG. 4 Influence of colloidal silica concentration on active agent recover rate (in vitro)

FIG. 4 illustrates that the concentration of colloidal silica also affected recovery rates of the active agent. It was found that as the concentration of colloidal silica (in this case Aerosil R972) increased from 1.75% to 3% w/w, the recovery rate was lowered.

Again, although the recovery profile slowed dramatically as the silica concentration increased from 1.75 to 3%, the viscosity only increased slightly from 90 mPas to 127 mPas.

Figure 5:
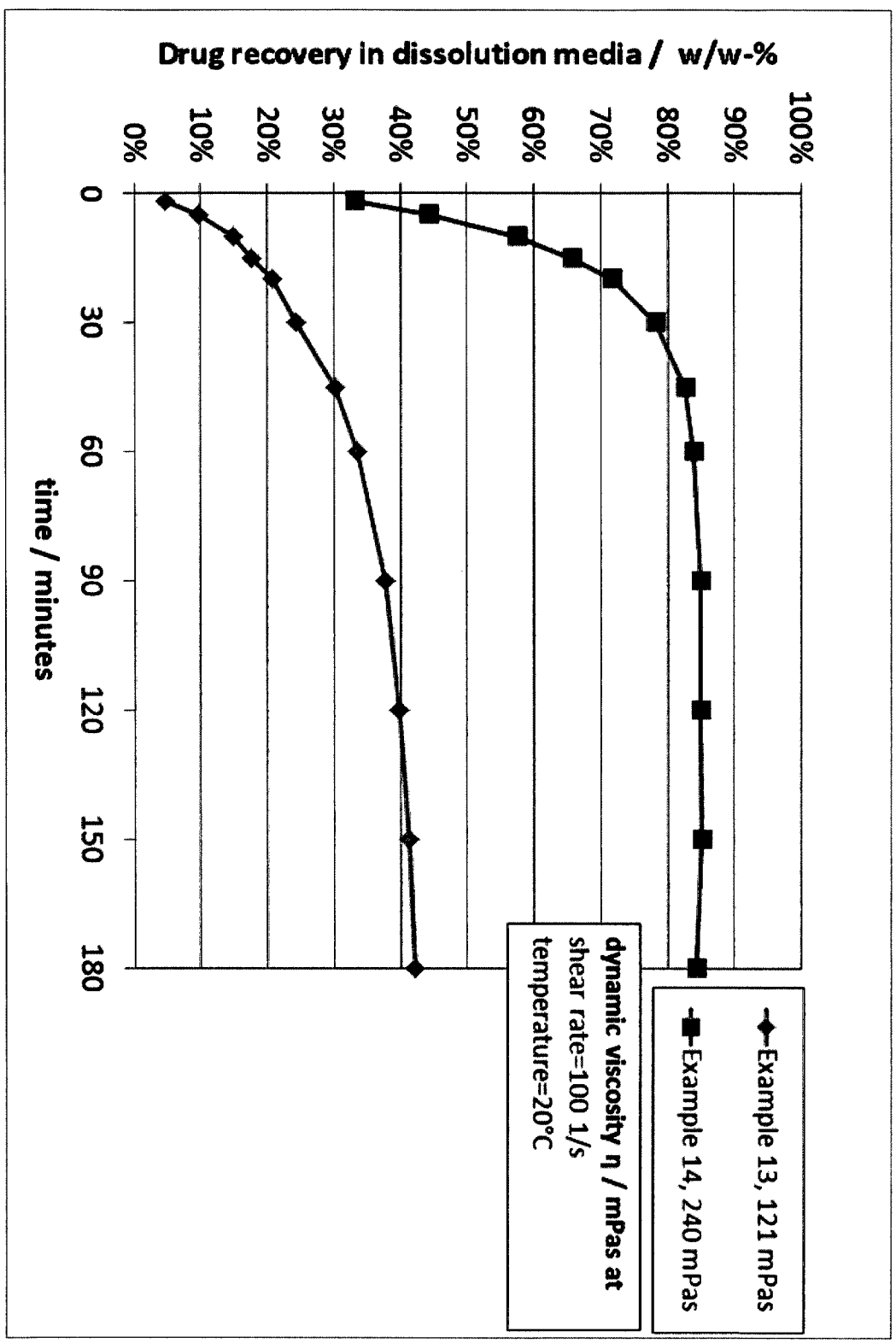
FIG. 5 Influence of colloidal silica type (hydrophobic vs hydrophilic) on active agent recovery rate (in vitro)

FIG. 5 illustrates that the type of colloidal silica may also affect the recovery rate of the active agent. Here, hydrophobic colloidal silica (Aerosil R972) is shown to significantly lower the recovery rate compared to hydrophilic colloidal silica (Aerosil 200). This is despite the hydrophobic silica imparting a lower viscosity on the composition compared to the same composition using hydrophilic silica. This is contrary to the common understanding in the art.

Figure 6:
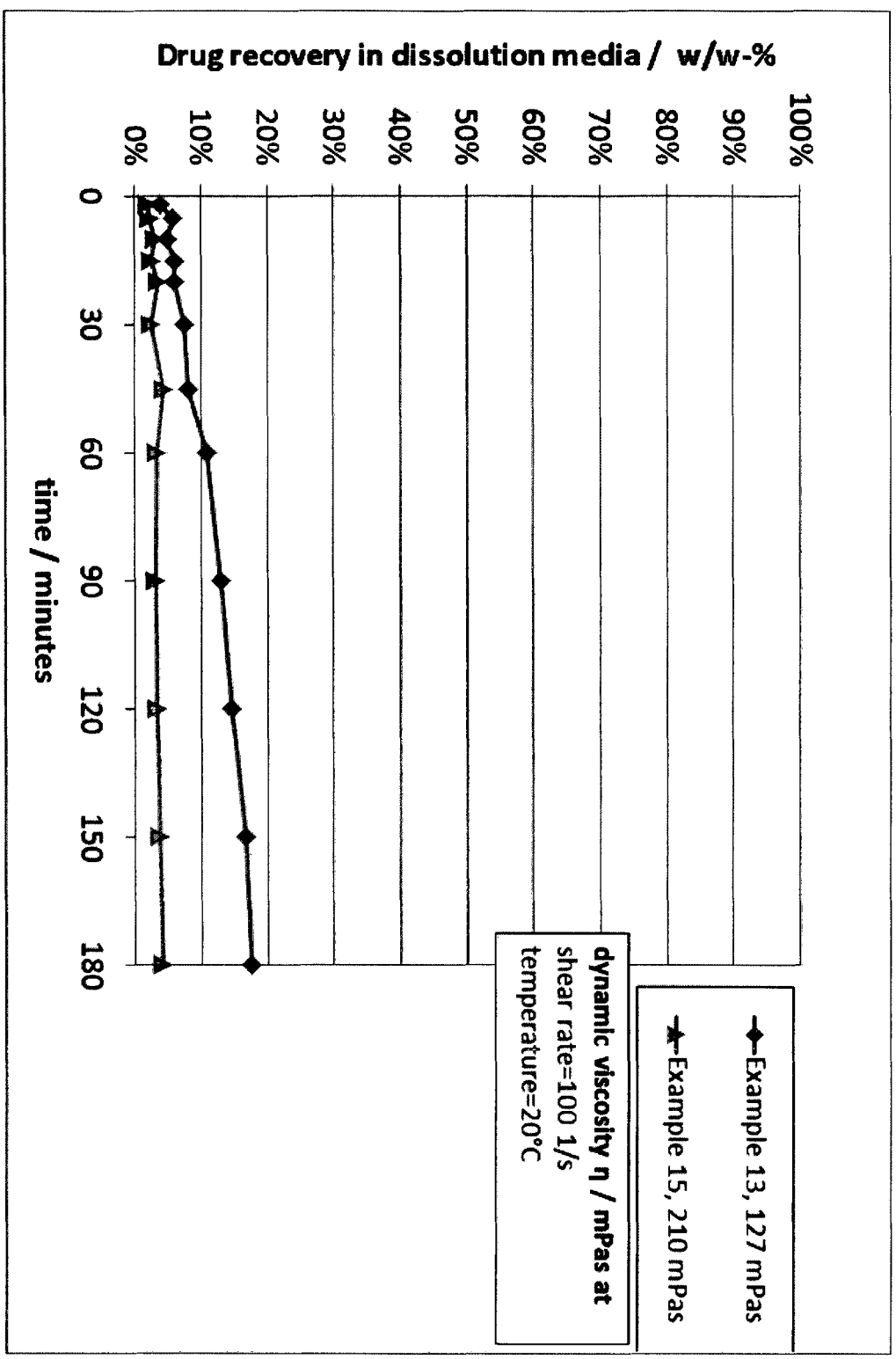
FIG. 6 Influence of oil on active agent recovery rate (in vitro)

FIG. 6 illustrates that the type of oil used may also affect the recovery rate of the active agent.

Figure 7:
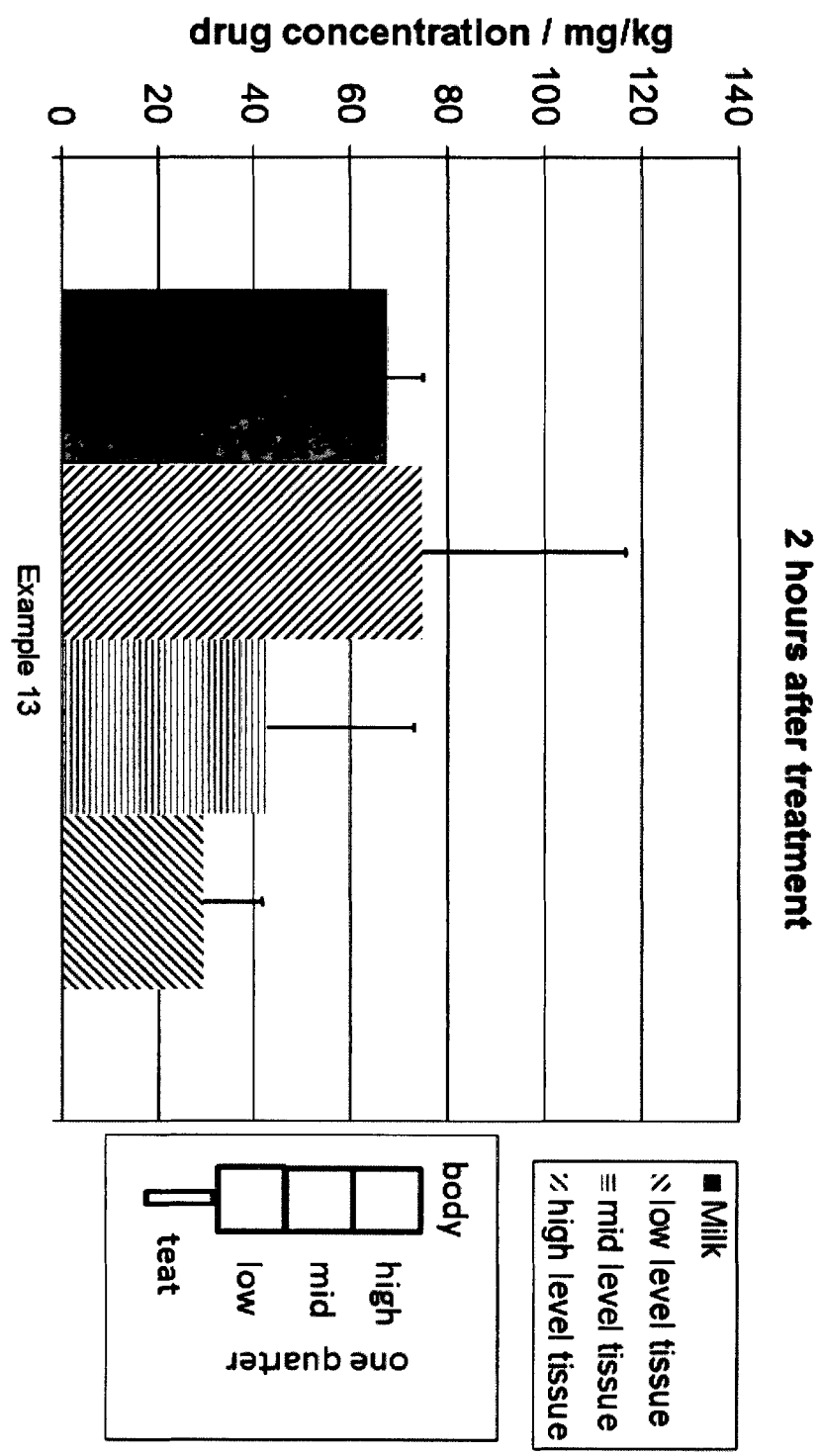
FIG. 7 Exemplification of cloxacillin bioavailability in tissues 2 hours after treatment (in vivo)

FIG. 7 illustrates the distribution of cloxacillin in different tissues two hours after treatment. In this case tissue is defined as remaining udder directly after milking, which includes extracellular liquid, blood vessels, and potentially some remaining milk which is not milked out.

Figure 8:
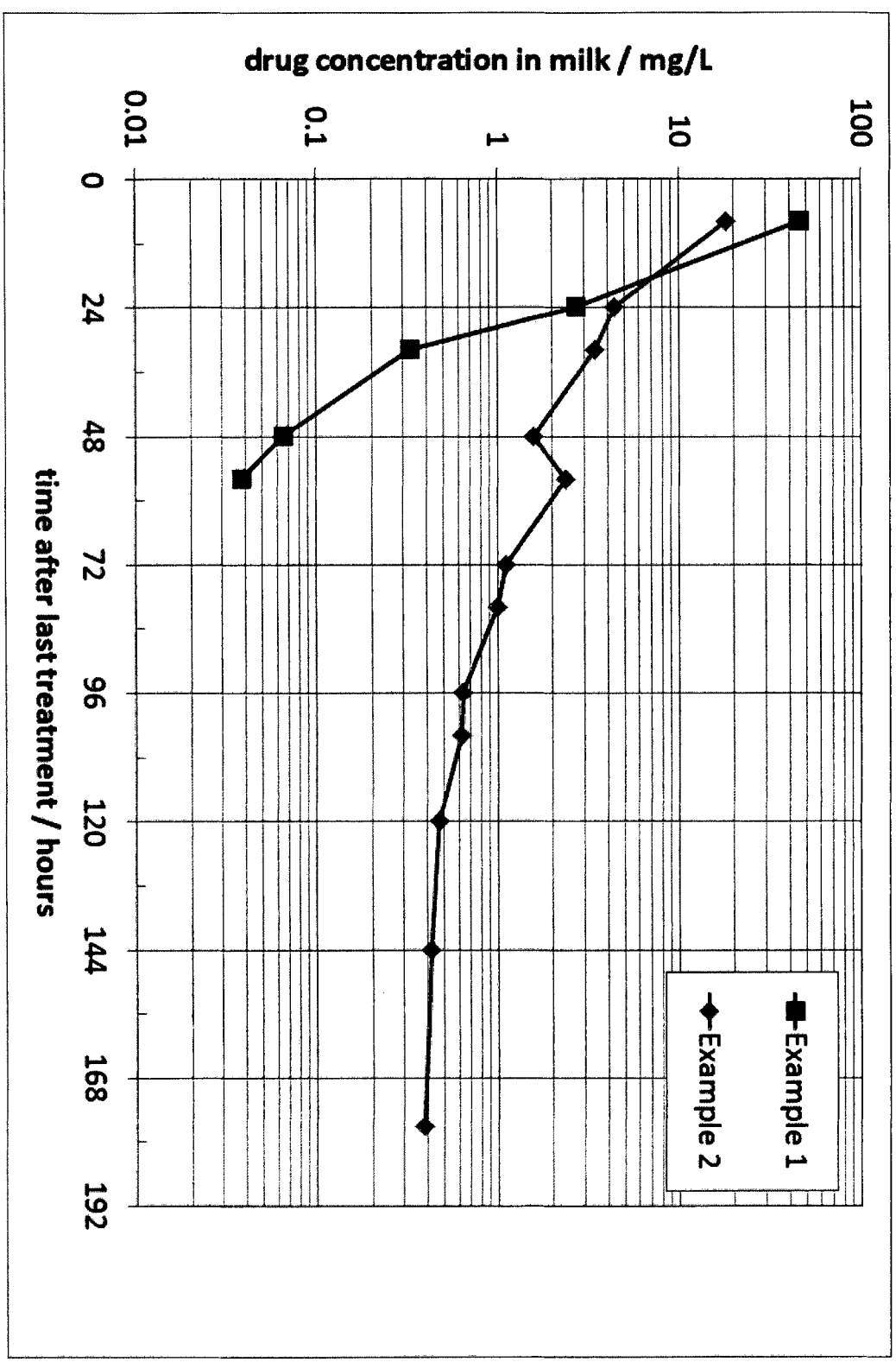
FIG. 8 Influence of active agent type on active agent concentration in milk (in vivo)
Figure 9:
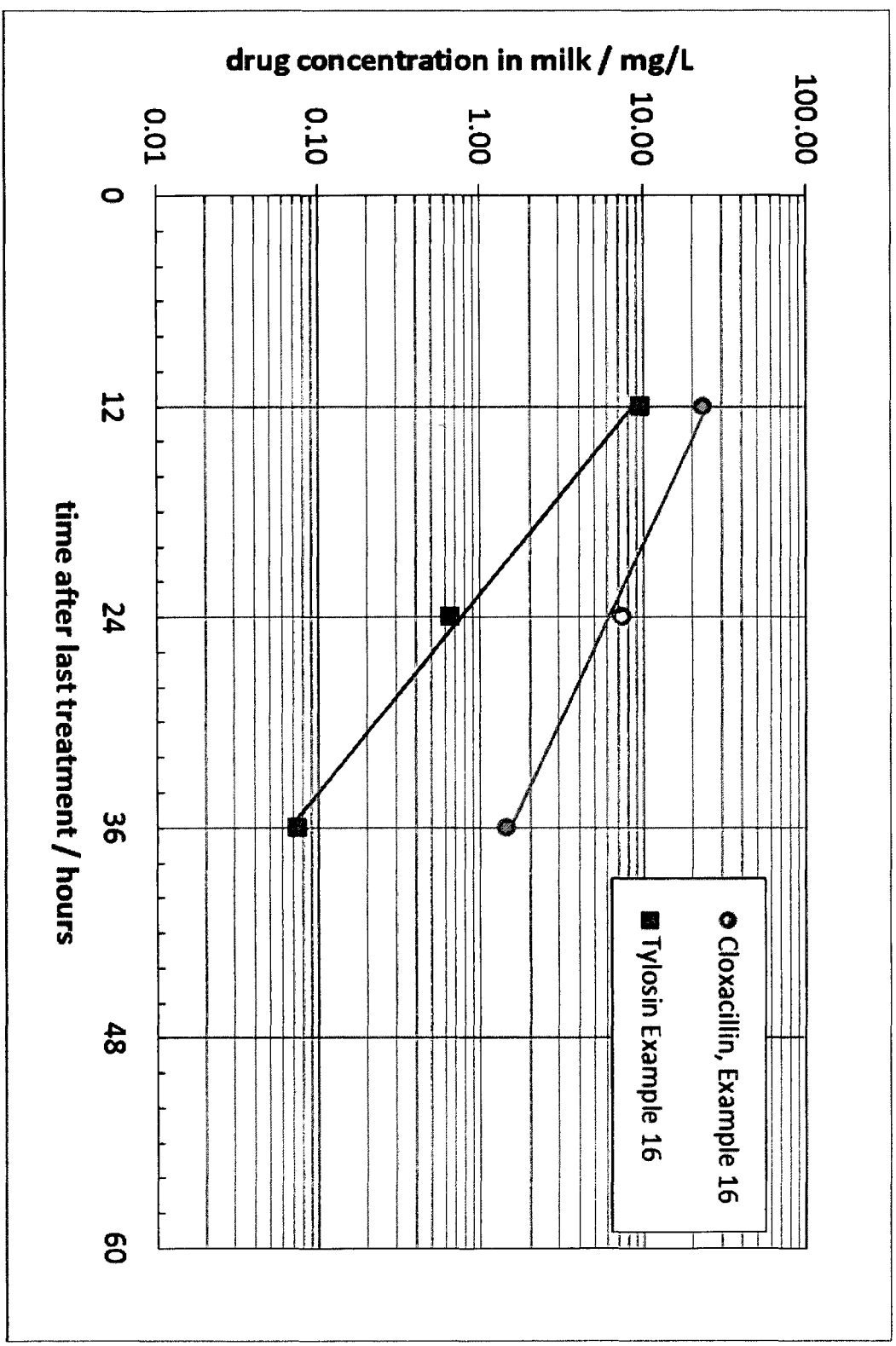
FIG. 9 Influence of active agent type on active agent concentration in milk (in vivo)

FIGS. 8 and 9 illustrates how different active agents can also have an affect on the release profile of the active agent itself, all else being substantially equal. In FIG. 8, when cloxacillin in the example composition 1 is replaced with cephapirin (as shown in example composition 2), the release profile is substantially slowed. In FIG. 9, differences were also seen between cloxacillin and tylosin. This was indeed a surprising result and suggests that the active's release may be influenced by an interaction with a possible structural network formed with some or all of the excipients in the composition's base.

FIGS. 10-14 illustrate how the WHP of the composition may be affected by the characteristics of the composition.

Figure 10:
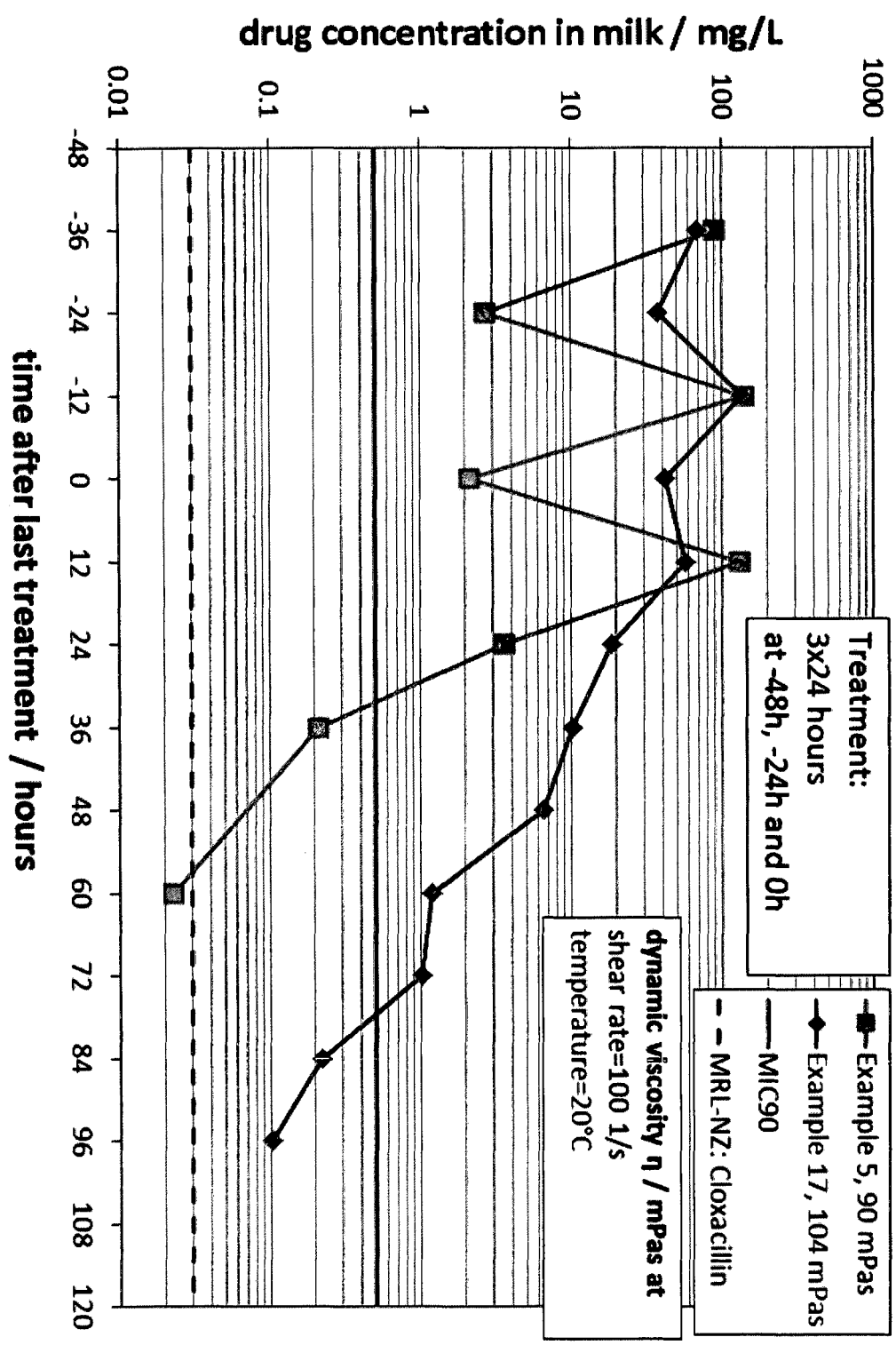
FIG. 10 Influence on composition characteristics on WHP (in vivo)

FIG. 10 illustrates how an increase in the amount of colloidal silica from 1.75% to 3.00% w/w can alter the WHP significantly.

Figure 11:
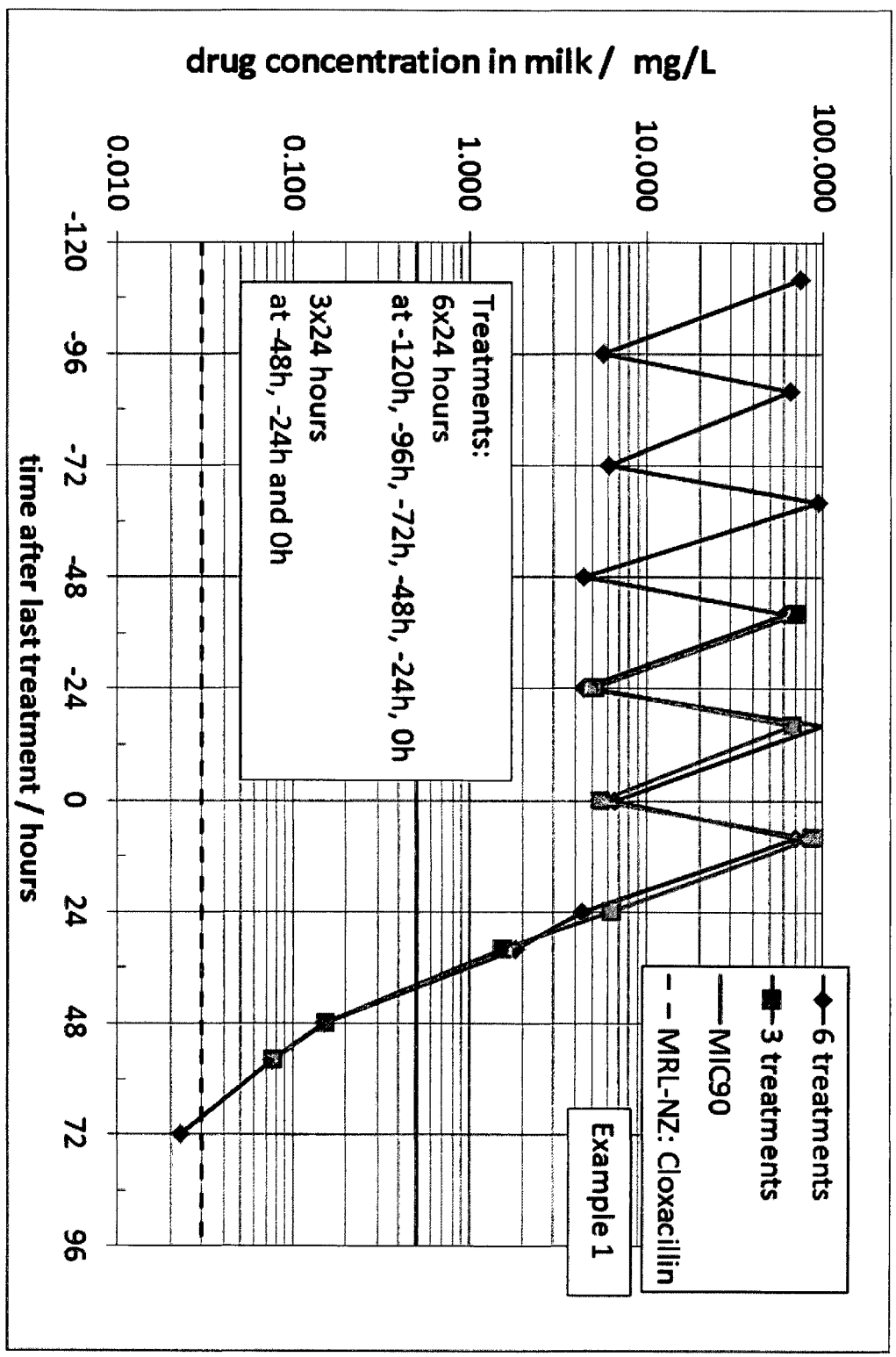
FIG. 11 Influence on the number of treatments of example composition 1 on WHP (in vivo)

FIG. 11 illustrates that the number of treatments does not affect WHP. The WHP is approximately equal regardless of whether the animal is treated with a 6×24 hour or 3×24 hour regime.

FIG. 12 illustrates the calculated WHP of example 1 composition according to ACVM (Agricultural Compounds & Veterinary Medicines) guidelines.

Figure 13:
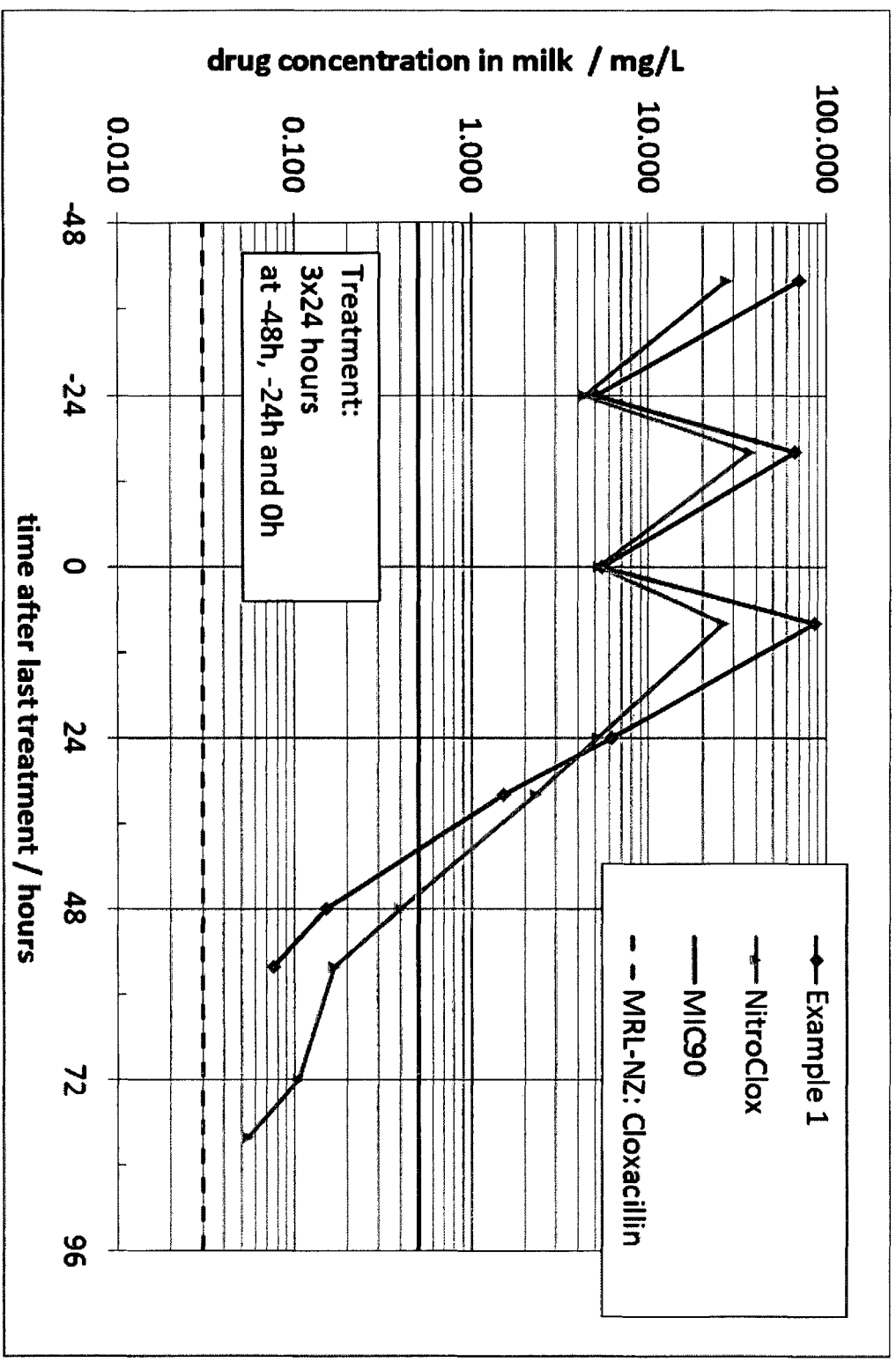
FIG. 13 Comparison of treatment between Example 1 composition and NitroClox™ LA (in vivo)

FIG. 13 illustrates the effectiveness of example 1 composition versus NitroClox™ LA. Of particular interest is that after each treatment, the amount of active agent is higher when administered with the example 1 composition than NitroClox™ LA, suggesting a higher bioavailability of example 1, 24 h after treatment. Similar to NitroClox™ LA, the example 1 composition does not decrease below the MIC90 (solid line) 24 h after treatment, yet is more rapidly removed from the milk after the final treatment at 0 hrs.

FIG. 14 reflects the results shown in FIG. 13. The example 1 composition is calculated to have a WHP of only 72 hours compared to 108 hours for NitroClox™ LA.

Figure 15:
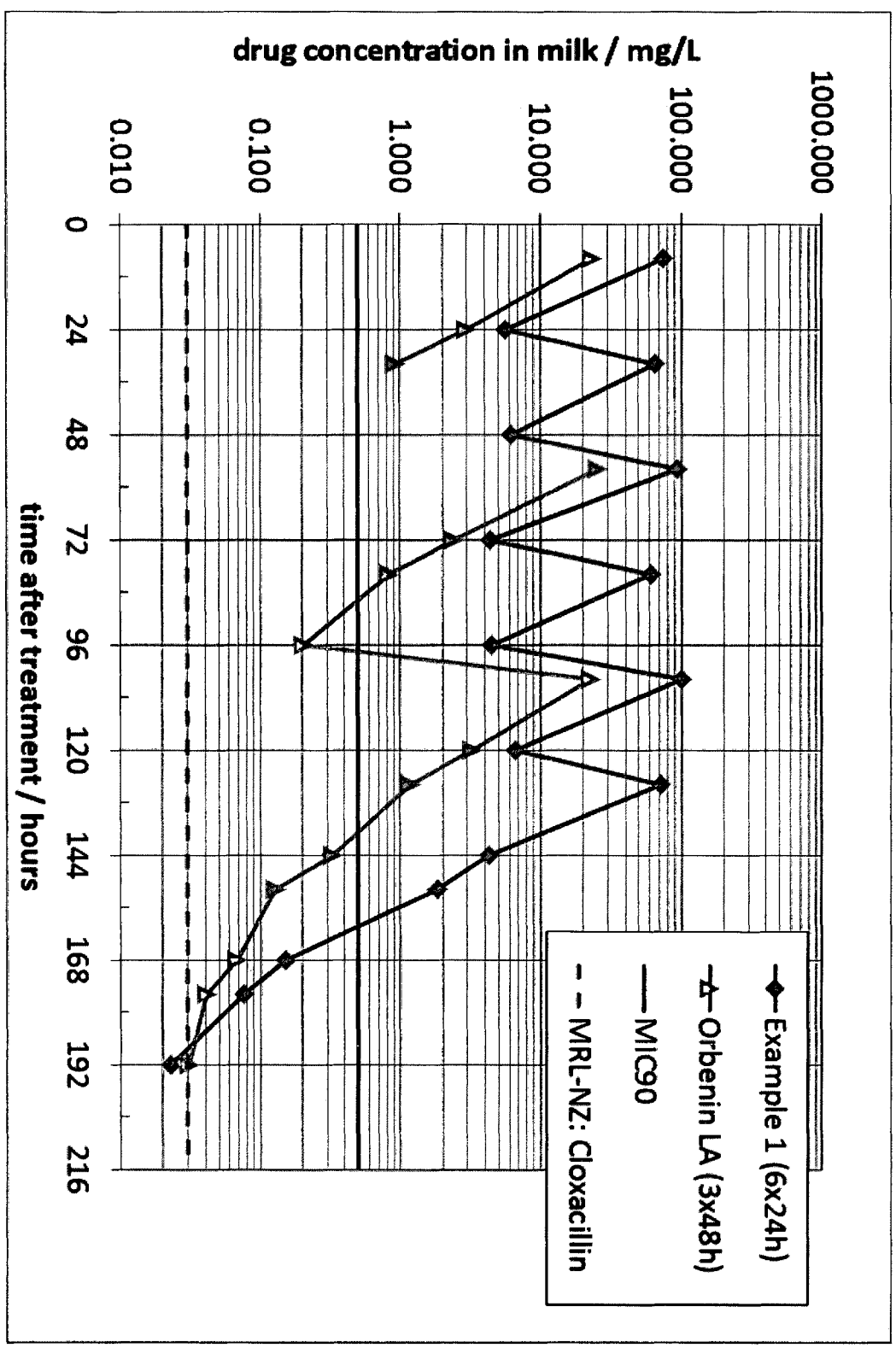
FIG. 15 Comparison of treatment between Example 1 composition and Orbenin™ LA (in vivo)

FIG. 15 compares the example 1 composition to Orbenin™ LA, albeit with a different treatment regime (6×4 hours vs. 3×48 hours, respectively). It can be seen that although the treatment regime using example 1 composition provides a much longer and consistent level of active agent in the milk than the treatment regime using Orbenin™ LA, the active agent is released from the milk much quicker after the final treatment. As can be seen, the final treatment of Orbenin™LA is at 96 hours, whereas the final treatment with example 1 composition is at 120 hours; providing a longer treatment period. FIG. 16 illustrates that the calculated WHP is 12 hours and 24 hours shorter in the example 1 composition's 6×24 hour treatment regime compared to Orbenin's 3×48 hour and 5×24 hour treatment regimes, respectively.

Part 3: Manufacturing Method
a) Mix Miglyol 812, methyl paraben, propyl paraben and Span 80 well to form homogeneous oil mixture.
b) Sterilise the mixture at 140° C. for 3 hours and then cool to room temperature.
c) In a separate container, load the required amount of Aerosil R972 Pharma.
d) Sterilise at 140° C. for 3 hours and then cool to room temperature.
e) Disperse and homogenise the cloxacillin sodium into the sterilised oil mixture.
f) Disperse the sterilised Aerosil R972 Pharma into the sterilised oil suspension.
g) Homogenise the mixture.

Part 3: Animal Study

As part of a study commenced in November 2011, the Example 18 formulation, as detailed below, was investigated for efficacy in the treatment of bovine mastitis.

Example 18

|  | mg | w/w-% |
|---|---|---|
| Cloxacillin sodium | 229.2 | 4.584* |
| Methyl paraben | 3.75 | 0.075 |
| Propyl paraben | 1.25 | 0.025 |
| Sorbitan mono-oleate (Span 80) | 25 | 0.5 |
| Hydrophobic silica (Aerosil R972 Pharma) | 87.5 | 1.75 |
| Fractionated coconut oil (Miglyol812N) | 4653.3 | 93.066 |
| Total | 5000 | 100 |

*5% overages added

The animals used in the study were dairy cows diagnosed with clinical mastitis. On day 0, milk samples were obtained for bacteriological analysis and the animals were treated with intramammary infusions of Example 18 three times, with each treatment 24 hours apart. The dose for each treatment was 200 mg of cloxacillin as the sodium salt.

On days 28 and 35, further milk samples were obtained for bacteriological analysis to determine the cure rate. A successful bacteriological cure required the animal to be clinically cured of mastitis, and for the pathogen identified in the day 0 sample to be absent in the day 28 and day 35 samples.

Interim results available as of 1 Nov. 2012, provided a bacteriological cure proportion of 69.6% when treated with Example 18, from ~100 cows enrolled with clinical mastitis, and with gram positive bacteria identified at the time of enrolment.

A comparable study is that reported by M D Wraight, *New Zealand Veterinary Journal* 51(1), 26-32, 2003 "A comparative efficacy trial between cefuroxime and cloxacillin as intramammary treatments for clinical mastitis in lactating cows on commercial dairy farms". In this study, 200 mg of cloxacillin in a long-acting formulation was administered as an intramammary every 48 hours for three treatments, which resulted in a bacteriological cure proportion of 64.3%.

The interim study results on Example 18 demonstrate high efficacy of compositions of the invention, even when compared to more intensive long-acting treatments using the same active. This indicates that obtaining an advantageous, shorter withhold period by using compositions of the invention, does not reduce or compromise the efficacy of the treatment.

Part 4: Formulation Stability

A stability study was conducted on three batches of Example 18. These batches were packed into 5 mL polyethylene syringes and stored at designated storage temperatures and humidity conditions of 25° C./60% RH, 30° C./65% RH and 40° C./75% RH. The physical and chemical characteristics of the batches were recorded at regular intervals as recommended by ACVM. Based on the stability data, at a storage temperature of 25° C. a shelf life of at least 18 months is expected.

Aspects of the present invention have been described by way of example only and it should be appreciated that modifications and additions may be made thereto without departing from the scope thereof as defined in the appended claims.

We claim is:

1. A controlled release composition comprising:
a therapeutically effective amount of at least one active agent, wherein the active agent is an antibiotic, at least one preservative, and
an excipient base that provides a controlled release of the at least one antibiotic,
wherein the excipient base consists of hydrophobic colloidal silicon dioxide at a concentration between 0.1-5% w/w;
at least one oil; and
at least one non-ionic surfactant, wherein the surfactant has a hydrophilic-hydrophobic balance (HLB) between 0.5 and 30, and wherein the concentration of surfactant is between 0.01 to 10% w/w;
wherein the viscosity of the composition is below 300 mPas at a shear rate of 100 1/s and at a temperature of 20° C., and wherein the composition does not contain hydroxystearin.

2. The composition as claimed in claim 1, wherein the at least one antibiotic is selected from the group consisting of a beta-lactam, penicillin, cephalosporin, aminoglycoside, quinolones, sulphonamides, tetracyclines and macrolide antibiotic.

3. The composition as claimed in claim 1, wherein the at least one antibiotic is selected from the group consisting of cloxacillin or a functional derivative thereof, tylosin or a functional derivative thereof, cephapirin or a functional derivative thereof, and combinations thereof.

4. The composition as claimed in claim 1, wherein the composition comprises at least two antibiotics or the at least one antibiotic and at least one non-antibiotic active agent.

5. The composition as claimed in claim 4, wherein the at least two antibiotics or the at least one antibiotic and at least one non-antibiotic active agent is selected from the group consisting of:
amoxicillin and clavulanic acid;
penicillin active agent and aminoglycoside;
cloxacillin and tylosin; and
an antibiotic and a non-steroidal anti-inflammatory drug.

6. The composition as claimed in claim 1, wherein the at least one antibiotic is micronised.

7. The composition as claimed in claim 1, wherein the colloidal silicon dioxide is fumed colloidal silicon dioxide.

8. The composition as claimed in claim 1, wherein the concentration of colloidal silicon dioxide is between 1-3% w/w.

9. The composition as claimed in claim 1, wherein the surfactant has a hydrophilic-hydrophobic balance (HLB) between 4 and 16.

10. The composition as claimed in claim 1, wherein the non-ionic surfactant is selected from the group consisting of sorbitan esters, polyoxyethylene sorbitan fatty acid esters, polyoxyethylene castor oil derivatives, polyoxyethylene stearates, polyethylene oxide monooleate and combinations thereof.

11. The composition as claimed in claim 1, wherein the ratio of colloidal silicon dioxide to surfactant in the base is between 1:100 and 500:1.

12. The composition as claimed in claim 1, wherein the ratio of colloidal silicon dioxide to surfactant in the base is between 1:5 and 6:1.

13. The composition as claimed in claim 1, wherein the base includes more than one surfactant.

14. The composition as claimed in claim 1, wherein the viscosity of the oil is between 1 to 100 mPas at 20° C.

15. The composition as claimed in claim 1, wherein the viscosity of the oil is less than 40 mPas at 20° C.

16. The composition as claimed in claim 1, wherein the oil is selected from the group consisting of medium chain triglycerides, light liquid paraffin, ethyl oleate and sesame oil.

17. The composition as claimed in claim 1, wherein the density of the oil is between 0.80 and 0.99 g/cm$^3$.

18. The composition as claimed in claim 1, wherein the composition has a viscosity below 150 mPas at a shear rate of 100 1/s and temperature of 20° C.

19. A method of manufacturing a composition as claimed in claim 1 comprising the steps of:
 a) mixing the oil and surfactant in a container to form a homogenous oil mixture;
 b) dispersing the active agent in the oil mixture; and
 c) subsequently adding the colloidal silicon dioxide to the oil mixture.

20. A method of treating a non-human animal in need thereof with a composition as claimed in claim 1 comprising administering the composition to the animal by intramammary infusion.

21. The method as claimed in claim 20 comprising administering 1-6 doses of 5 g formulation composition over a period of 0 to 120 hours administered 3×24 hours or 6×24 hours.

22. The method as claimed in claim 20 for the treatment or prevention of mastitis during the lactation period of a non-human animal.

23. The composition as claimed in claim 1, which is non-aqueous.

24. The composition as claimed in claim 1, which comprises from 2 w/w-% to 9.18 w/w-% of the at least one antibiotic.

25. The composition as claimed in claim 1, wherein the at least one antibiotic is cloxacillin or a functional derivative thereof.

26. The composition as claimed in claim 1, wherein the composition maintains the minimum inhibitory concentration wherein 90% of the microbes are killed (MIC90) during the entire treatment period until the next dose.

* * * * *